(12) United States Patent
Bae

(10) Patent No.: US 6,614,409 B1
(45) Date of Patent: Sep. 2, 2003

(54) GLARE SHIELDING DEVICE OF WELDING HELMET AND METHOD OF CONTROLLING THE SAME

(75) Inventor: Young-Dawn Bae, Suwon (KR)

(73) Assignee: Otos Co., Ltd. (KR)

( * ) Notice: Subject to any disclaimer, the term of this patent is extended or adjusted under 35 U.S.C. 154(b) by 74 days.

(21) Appl. No.: 09/721,173

(22) Filed: Nov. 22, 2000

(30) Foreign Application Priority Data

Nov. 23, 1999 (KR) ......................................... 1999-52109
Oct. 12, 2000 (KR) ......................................... 2000-59958

(51) Int. Cl.$^7$ ............................. G09G 5/00; B23K 9/10; H01J 40/14; A42B 1/00; G02F 1/1335
(52) U.S. Cl. ...................... 345/8; 219/130.01; 250/205; 250/215; 349/14; 349/16; 2/8
(58) Field of Search ........................... 345/7, 8; 349/14; 2/7, 8, 9; 219/130.01; 250/205; 323/906; 320/101; 368/205; 136/291

(56) References Cited

U.S. PATENT DOCUMENTS 5,248,880 A * 9/1993 Fergason .................... 250/205
5,252,817 A * 10/1993 Fergason et al. ............ 250/205
5,347,383 A * 9/1994 Fergason ...................... 359/85
5,533,206 A * 7/1996 Petrie et al. ........................ 2/8
5,751,258 A * 5/1998 Fergason et al. ................ 345/7
6,067,129 A * 5/2000 Fergason ...................... 349/14
6,097,451 A * 8/2000 Palmer et al. ................. 349/14
6,230,327 B1 * 5/2001 Briand et al. ................... 345/8
6,242,711 B1 * 6/2001 Cooper ................... 219/130.01

* cited by examiner

Primary Examiner—Bipin Shalwala
Assistant Examiner—David L. Lewis
(74) Attorney, Agent, or Firm—Cantor Colburn LLP

(57) ABSTRACT

The present invention discloses a glare shielding device. The glare shielding device includes a microprocessor for controlling an activation time and a driving time of a liquid crystal panel. The microprocessor generates an activation control signal of a liquid crystal activating portion, a driving control signal of a liquid crystal driving portion, and a power off control signal in response to a simultaneous detection of a welding light and a high frequency generated during a welding process. The liquid crystal activating portion becomes a floating state in a standby mode and activates the liquid crystal panel using a minus voltage between a high voltage and an activation voltage. The liquid crystal driving portion becomes a floating state in a standby mode and drives the liquid crystal panel in response to the driving control signal.

7 Claims, 3 Drawing Sheets

GLARE SHIELDING DEVICE OF WELDING HELMET AND METHOD OF CONTROLLING THE SAME

CROSS REFERENCE

This application claims the benefit of Korean Patent Application No. 1999-52109, filed on Nov. 23, 1999, and the benefit of Korean Patent Application NO. 2000-59958, field on Oct. 12, 2000, under 35 U.S.C. §119, the entirety of which is hereby incorporated by reference.

BACKGROUND OF THE INVENTION

1. Field of the invention

The present invention relates to a glare shielding device of a welding helmet and a method of controlling the same.

2. Description of Related Art

In recent, glare shielding devices are widely used in the welding and cutting torch technology in order to protect eyes of workers. With such glare shielding devices the radiation above 780 nm (infrared) and below 365 nm (ultraviolet) are filtered and only the radiation in the visible range is dimmed, so that workers can discriminate a welding position of a specific spot.

U.S. Pat. No. 5,315,099 (German Patent No. 2,606,416) discloses a glare shielding device which includes an electro-optical glare shield having at least one liquid crystal cell; an electronic circuit connected to the electro-optical glare shield for applying an electric operating voltage thereto for varying an optical transmission value of the at least one liquid crystal cell; and a light sensor connected to the electronic circuit for providing an input signal thereto indicative of sensed light adjacent to the electro-optical glare shielding device.

U.S. Pat. No. 5,444,232 (European Patent No. 630,627) discloses an antiglare device which includes a protective light filter, a photosensor detector electronics adapted to produce a dimming signal, evaluating electronics which control an electro-optical protective light filter, a controller to control the brightening time of the protective light filter, the controller detecting at least the intensity of the light impinging on the sensor; the controller being objectively connected to a timing generator to detect at least the duration of the dimming signal produced by the detector electronics; and the controller including means to interlink the acquired data with respect to logic and/or time.

The antiglare device disclosed in U.S. Pat. No. 5,444,232 detects the absolute light intensity, the respective amount of light and the welding duration, and interconnects these parameters in a meaningful manner with respect to logic and/or time by means of suitable electronics, thereby optimizing the brightening time to the given circumstances.

Such a glare shielding device has an advantage that a circuit construction is simple. However, it has the following disadvantages. Firstly, a time delay occurs between an input of welding light and an operation of the antiglare device. Secondly, power consumption is high due to an operation of a control circuit having a microcomputer for continuously detecting a variation of an input welding light. Thirdly, in case of the device providing an automatic turn off function in order to prevent a continuous power consumption, a switch should be turned on by a manual actuation in order to operate the device again. This is a troublesome task. Fourthly, a photosensitivity of the input welding light should be controlled depending on a welding condition. Fifthly, in case that a welding signal is detected using only a light signal, since detected signals depend on a welding method and a welding machine, the glare shielding device may abnormally operate.

In order to overcome the problems described above, a glare shielding device using a non-optical detection means has been introduced. In this case, since a continuous light shielding phenomenon may occur due to a non-intended abnormal operation that may be generated by a latent magnetic filed in surroundings, workers can not discriminate welding light due to the continuous light shielding phenomenon, whereupon workers can not check a welding state. For example, a spark during a welding process may generate a magnetic field.

For the forgoing reasons, there is a need for a glare shielding device that can minimize a power consumption and that worker can check a welding state during a welding process.

SUMMARY OF THE INVENTION

To overcome the problems described above, preferred embodiments of the present invention provide a glare shielding device that can minimize a power consumption and that worker can check a welding state during a welding process.

In order to achieve the above object, the preferred embodiments of the present invention provide a glare shielding device for a welding helmet having a liquid crystal panel. A solar battery circuit converts light into an electrical energy to output first and second output voltages. A charging circuit charges the first output voltage to provide a driving voltage. An oscillator circuit generates an oscillating signal in response to the second output voltage. A high-voltage amplifier charges-pumps the driving voltage in response to the oscillator circuit to generate a high voltage. A regulator regulates the high voltage to generate a stable driving voltage. An activation voltage generator generates a liquid crystal activation voltage in response to the oscillating signal. A driving circuit power controller generates a ground voltage by being switched from a standby mode to a driving mode in response to a light detection signal, and maintains a floating state by being switched from the driving mode to the standby mode in response to a power off controlling signal. A light detector detects a welding light using the second output voltage as a power source, and outputs the light detection signal using the driving voltage as a power source. A high-frequency detector detects a high-frequency generated during a welding process using the light detection signal as a power source, and outputs a high-frequency detection signal using the liquid crystal driving control signal as a power source. A liquid crystal activating portion activats the liquid crystal panel using a minus voltage between the high voltage and the liquid crystal activation voltage in response to the light detection signal, and maintains an activation action during a predetermined period in response to the activation controlling signal. A liquid crystal driving portion drives the liquid crystal panel using a minus voltage between the liquid crystal driving voltage and a ground voltage in response to the oscillator circuit. A controller works in response to the light detection signal, generates the activation controlling signalduring an initial activation time in response to the high-frequency detection signal, generates the driving control signalafter the initial activation time passes, stops generating the driving control signal and generating the power off control signal and performs the standby mode when the light detection signal and the high-frequency detection signal does not exist.

The charging circuit includes a charging battery for charging the first output voltage; a plurality of light emitting diodes for being connected both terminals of the charging battery and preventing an overcharge; and a smooth capacitor for smootting an output voltage of the battery to output the driving voltage. The regulator includes an adjusting means for adjusting a level of the liquid crystal driving voltage to adjust a light transmittance of the liquid crystal. The glare shielding device further includes a temperature detector for detecting a temperature of the liquid crystal panel, wherein the activation voltage generator adjusts a level of the liquid crystal activation voltage in response to a temperature control signal and outputs it, and the controller outputs the temperature control signal in response to a temperature detection of the temperature detector.

The preferred embodiment of the present invention further provides a method of controlling a glare shielding device for a welding helmet. The method includes, in a standby mode, generating first and second output voltages by converting ambient light into an electrical energy using a solar battery, generating a driving voltage of a predetermined level by charging the first output voltage, generating a high voltage and an activation voltage by charge-pumping the driving voltage in response to the second output voltage, and for maintaing a liquid crystal activating portion and a liquid crystal driving portion to be in a floating state; detecting a welding light; switching the liquid crystal activating portion and the liquid crystal driving portion to a driving mode by releasing the floating state, and activating a liquid crystal panel through the liquid crystal activating portion using a minus voltage between the high voltage and the activation voltage; detecting a high frequency generated during a welding process; driving the liquid crystal panel through the liquid crystal driving portion by finishing an activation time of the liquid crystal activating portion when the high frequency; and switching the liquid crystal activating portion and the liquid crystal driving portion to the standby mode when the high frequency and the welding light are not detected.

At this point, a level of the activation voltage varies according to an ambient temperature of the liquid crystal panel to rapidly activate the liquid crystal panel.

The preferred embodiment of the present invention provides a glare shielding device for a welding helmet. The glare shielding device includes a liquid crystal panel. A solar battery circuit converts light into an electrical energy to output first and second output voltages. A charging circuit charges the first output voltage to provide a driving voltage. An oscillator circuit generates an oscillating signal in response to the second output voltage. A high-voltage amplifier charge-pumps the driving voltage in response to the oscillator circuit to generate a high voltage. A delay time setting portion sets an off time of the liquid crystal display panel. A reset circuit generates a reset signal by a switching of a reset switc. A regulator regulates the high voltage to generate a stable driving voltage. An activation voltage generator generates a liquid crystal activation voltage in response to the oscillating signal. A driving circuit power controller generates a ground voltage by being switched from a standby mode to a driving mode in response to a light detection signal, and maintains a floating state by being switched from the driving mode to the standby mode in response to a power off controlling signal. A light detector detects a welding light using the second output voltage as a power source, and outputs the light detection signal using the driving voltage as a power source. A high-frequency detector detects a high-frequency generated during a welding process using the light detection signal as a power source, and outputs a high-frequency detection signal using the liquid crystal driving control signal as a power source. A liquid crystal activating portion activats the liquid crystal panel using a minus voltage between the high voltage and the liquid crystal activation voltage in response to the light detection signal, and maintains an activation action during a predetermined period in response to the activation controlling signal. A liquid crystal driving portion drives the liquid crystal panel using a minus voltage between the liquid crystal driving voltage and a ground voltage in response to the oscillator circuit. A controller is reset in response to the reset signal and performing a self-test mode, works in response to the light detection signal, generates the activation controlling signalduring an initial activation time in response to the high-frequency detection signal, generates the driving control signal after the initial activation time passes, stops generating the driving control signal and generates the power off control signal, and performs the standby mode when the light detection signal and the high-frequency detection signal does not exist.

Using the glare shielding device according to the preferred embodiment of the present invention, a power consumption can be minimized and worker can check a welding state during a welding process. Further, since by detecting an ambient temperature and compensating an activation voltage in light that response characteristics is lowered at a low temperature, an initial glare shielding effect can be improved.

BRIEF DESCRIPTION OF THE DRAWINGS

For a more complete understanding of the present invention and the advantages thereof, reference is now made to the following descriptions taken in conjunction with the accompanying drawings, in which like reference numerals denote like parts, and in which.

DETAILED DESCRIPTION OF PROFFERED EMBODIMENTS

Reference will now be made in detail to a preferred embodiment of the present invention, example of which is illustrated in the accompanying drawings.

Figure 1:
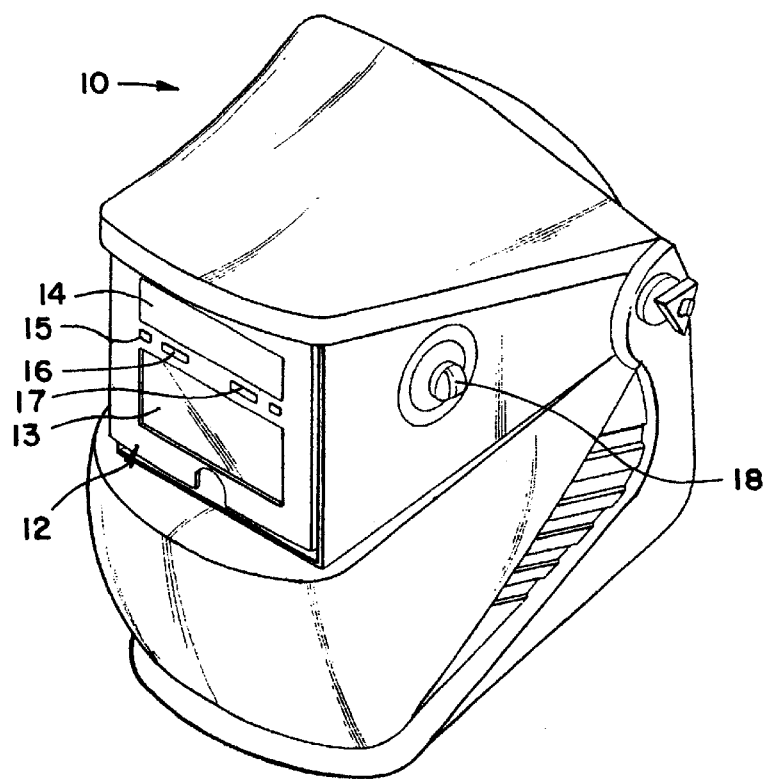
FIG. 1 is a perspective view illustrating a welding helmet having a glare shielding device according to a preferred embodiment of the present invention.

FIG. 1 is a perspective view illustrating a welding helmet according to the preferred embodiment of the present invention. As shown in FIG. 1, the welding helmet includes a glare shielding plate 12 arranged on a front surface thereof. The glare shielding plate 12 is made of a noncombustible plastic material that is a relatively light-weight material. The glare shielding plate 12 includes a liquid crystal panel 13, a solar battery 14, a photosensor 15, an antenna 16, and a temperature sensor 17. The welding helmet 10 further includes a first adjusting knob 18 arranged on its side surface. The first adjusting knob 18 serves to adjust a level of a driving voltage of a liquid crystal. A light filter is attached on a surface of the liquid crystal panel 13, so that only the visible ray can be transmitted.

Figure 2:
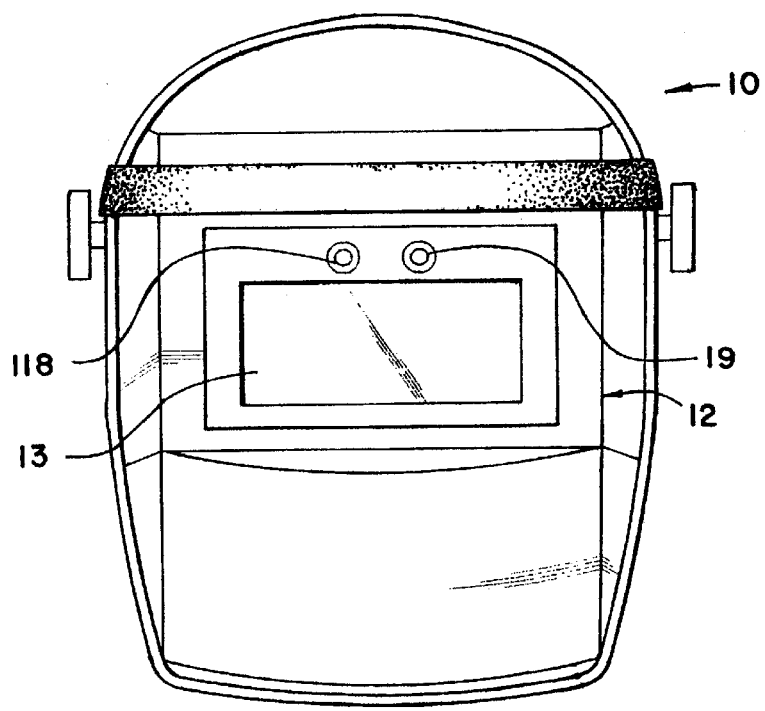
FIG. 2 is a back view illustrating the welding helmet having the glare shielding device according to the preferred embodiment of the present invention.

FIG. 2 is a back view illustrating the welding helmet according to the preferred embodiment of the present invention. As shown in FIG. 2, a reset switch 19 and a second adjusting knob 118 are arranged at a back surface of the welding helmet 10. The second adjusting knob 118 serves to adjust a time delay.

The liquid crystal panel 13 is made of a transparent material and thus a worker with the welding helmet 10 can observe his surroundings. The photosensor 15 and the antenna 16 detects a welding light and a high-frequency signal generated during a welding process to control a transmitted amount of the welding light. Therefore, a glare due to the welding light is effectively shielded, and at the same time workers can observe the welding state.

The temperature sensor 17 serves to make the liquid crystal panel 13 to properly work in the early stage even though an ambient temperature becomes lowered.

Figure 3:
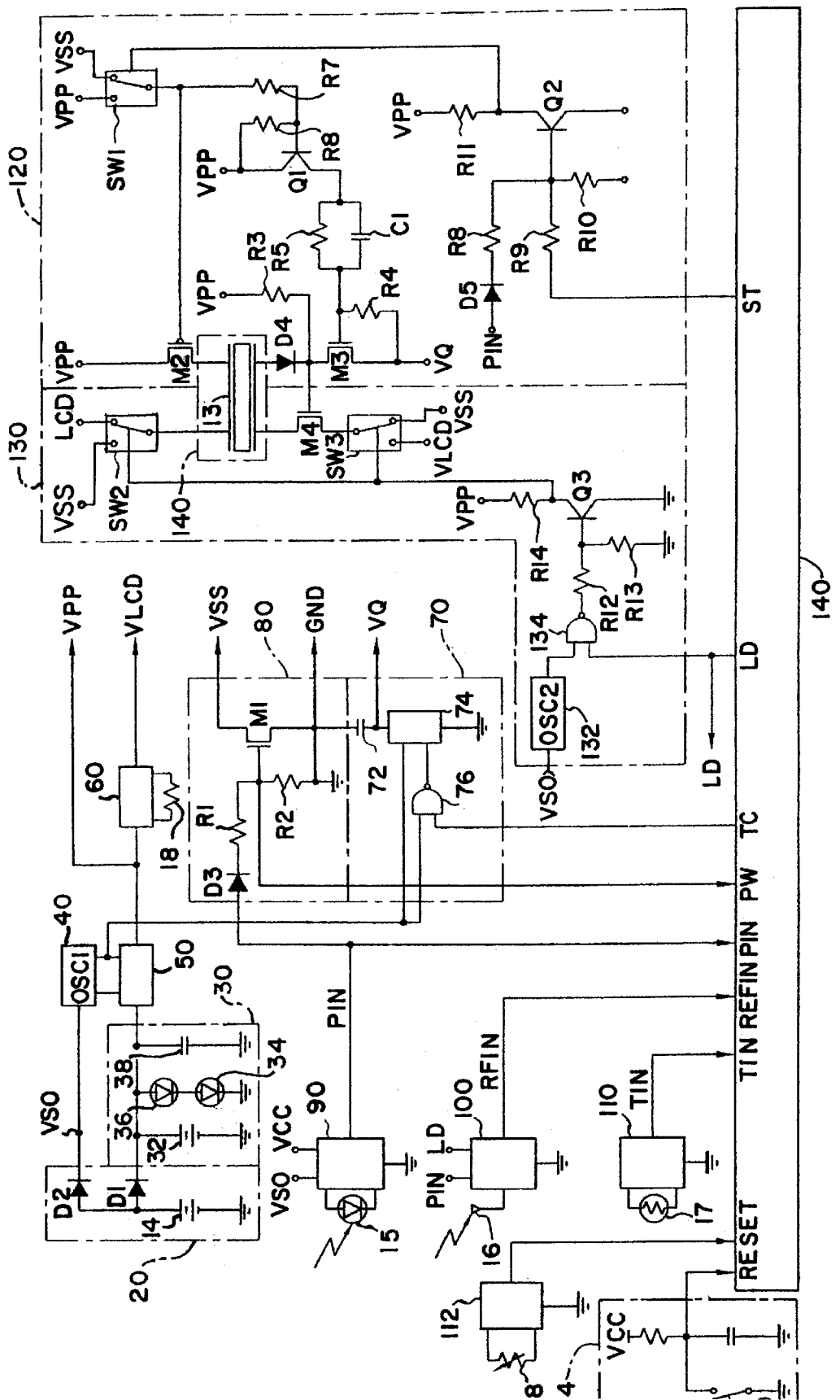
FIG. 3 is a circuit diagram illustrating the glare shielding device according to the preferred embodiment of the present invention.

FIG. 3 is a circuit diagram illustrating a glare shielding device according to the preferred embodiment of the present invention. As shown in FIG. 3, the glare shielding device includes a solar battery circuit 20, a charging circuit 30, an oscillator circuit 40, a high voltage generator 50, a regulator 60, an activation voltage generator 70, a driving circuit power controller 80, a light detector 90, a high-frequency detector 100, a temperature detector 110, a delay time setting portion 112, a reset circuit 114, a liquid crystal activating portion 120, a liquid crystal driving portion 130, and a controller 140.

The solar battery circuit 20 provides a voltage generated by the solar battery 14 to a charging circuit 30 through a diode D1 as a first output voltage, and through a diode D2 as a second output diode D2, respectively.

The charging circuit 30 includes a charging battery 32, light emitting diodes 34 and 36, a smooth capacitor 38. The light emitting diodes 34 and 36 serve to prevent an overcharge of the solar battery 32. In other words, the light emitting diodes 34 and 36 change the electrical energy into the light energy when a forward voltage of greater than a predetermined level is applied, so that an overcharge is prevented. Through the smooth capacitor 38, a driving voltage (VCC) having a constant level is output. Even though not shown, it is preferable that the charging circuit 30 includes a capacitor for removing a noise.

The oscillator circuit 40 includes a NAND gate, a resistance, and a capacitor that are not shown, and generates an oscillating signal and an inverted signal having a phase inverted by 180°, which have a frequency that is determined by a resistance at a high state of a VSO that is applied to an input terminal of the NAND gate and a time constant of a capacitor.

The high voltage generator 50 generates a high voltage (VPP) that drives a liquid crystal by inputting the oscillating signal and the inverted signal and then charge-pumping the driving voltage (VCC).

The regulator 60 regulates a high voltage (VPP) to output a liquid crystal driving voltage (VLCD) having a stable certain level. An output level of the liquid crystal driving voltage is adjusted by the adjusting knob 18.

The activation voltage generator 70 includes a charge capacitor 72 connected between the ground and the output terminal of an activation voltage (VQ), a charge-pump circuit 74 connected between the output terminal of the activation voltage and the ground, and a gate 76. The gate 76 gates the oscillating signal of the oscillator circuit 40 in response to a temperature detection control signal (TC). The charge-pump circuit 74 charge-pumps electrical charges to the capacitor 72 in response to the oscillating signal of the oscillator circuit 40 to generate a negative activation voltage (VQ). Further, the charge-pump circuit 74 generates an activation voltage of the higher level as the charge-pump unit cell becomes increased in number. In other words, when a temperature of the liquid crystal panel falls below a certain temperature set in advance, response characteristics of the liquid crystal may become bad and thus an initial activation may become slow. Therefore, to compensate the response characteristics of the liquid crystal depending on the temperature of the liquid crystal panel, it is preferred that the higher activation voltage is supplied.

The driving circuit power controller 80 includes a diode D3, resistances R1 and R2, and an NMOS transistor M1. The NMOS transistor M1 has a gate electrically connected to a power off control signal PW and a light detecting signal PIN through the diode D3 and the resistance R1. The NMOS transistor M1 further has a drain connected to a ground voltage VSS and a source connected to a ground. The NMOS transistor M1 is in an on state by the PIN signal and is in a floating state by the VSS signal. The NMOS transistor M1 is in an off state by the PW signal and is in a floating state by the VSS signal.

The light detector 90 operates the photosensor 15 to detect the welding light and outputs the light detecting signal PIN detected by the VCC voltage. Therefore, the light detecting signal PIN is output to have the same level as the VCC voltage.

The high-frequency detector 100 operates the antenna 16 using the PIN voltage to detect a high frequency generated during a welding process. Therefore, the high-frequency detecting signal RFIN is light-detected and is output during a normal action after the liquid crystal is activated The temperature detector 110 detects an ambient temperature of the liquid crystal panel using the temperature sensor 17 to output a temperature detecting signal TIN.

The delay time setting portion 112 set an off time t3 depending on a resistance value set by the adjusting knob 118. The off time t3 can be set from 80 ms to 500 ms when the light detection is not carried out.

The reset circuit 114 generates a reset pulse when the reset switch is in an on state to provide the controller with it.

The liquid crystal activating portion 120 includes a PMOS transistor M2, an NMOS transistor M3, a PNP transistor Q1, an analog switch SW1, resistances R3 to R11, and diodes D4 and D5. The analog switch SW1 contacts a VSS only to become an off state. In other words, in order to become an on state, the analog switch SW1 contacts a VPP.

The liquid crystal activating portion 120 becomes an on state by a transistor Q2. In other words, the analog switch SW1 is in an off state by an output of a collector of the transistor Q2, and the analog switch SW1 selects the VSS. The VSS signal turns on the PMOS transistor M2 to supply a VPP voltage to an upper electrode of the liquid crystal panel 13. The VSS signal is also applied to a base of the transistor Q1 and turns on it. An output of a collector of the transistor Q1 become a high state so that the NMOS transistor M3 is turned on. Therefore, a VQ voltage is applied to a lower electrode of the liquid crystal panel 13 through the NMOS transistor M3. As a result, when the liquid crystal is activated, a high voltage of VPP−VQ, i.e. a minus voltage between VPP and VQ, is applied to the two electrodes of the liquid crystal panel 13, thereby bring about excellent response characteristics. That is, since a high activation voltage is applied to the liquid crystal panel 13 at the beginning of a welding process, the liquid crystal panel 13 gets to immediately shield the welding light, thereby preventing the initial glare.

The liquid crystal activating portion 120 maintains an activation during a predetermined period by an activation control signal ST after an activation of the liquid crystal. When the set activation time passes, the ST signal becomes a low state and, thus the transistor Q2 is turned off. In response to this, the analog switch SW1 is turned off to output the VPP signal, whereupon the PMOS transistor M2 and the NMOS transistor M3 are all turned off. As a result, the activation voltage is not applied, whereby even though the PIN signal is continuously applied, since the ST signal maintains to be in a low state, the transistor Q2 is not turned on.

The liquid crystal driving portion 130 includes an NMOS transistor M4, an NPN transistor Q3, analog switches SW2 and SW3, resistances R12 to R14, an oscillator circuit 132, and a NAND gate 134. The analog switch SW2 selects a VLCD to be in an off state and a VSS to be in an off state. The analog switch SW3 selects a VSS to be in an off state and a VLCD to be in an on state.

The oscillator circuit 132 has a construction similar to the oscillator circuit 40 and generates an oscillating signal having a predetermined frequency by a RC time constant when a VSO signal becomes a high state.

When a liquid crystal driving signal LD becomes a high state, the oscillating signal is output through the NAND gate 134. The transistor Q3 repeats to switch the analog switches SW2 and SW3 to on and off states through a predetermined frequency, whereby an AC voltage of VLCD-VSS whose phase is inverted to be a predetermined frequency is applied to the two electrodes of the liquid crystal panel 13. As a result, a light transmittance of the liquid crystal panel 13 is controlled in response to a VLCD level while the liquid crystal is driven.

When the liquid crystal driving signal LD becomes a low state, since an output of the oscillator circuit is intercepted in the NAND gate 134, the liquid crystal panel is not driven. At this point, when the liquid crystal panel is not driven, since the VSS voltage becomes a floating state and thus the liquid crystal activating portion 120 and the liquid crystal driving portion 130 maintains a floating state, a power consumption gets to be lowered.

Figure 4:
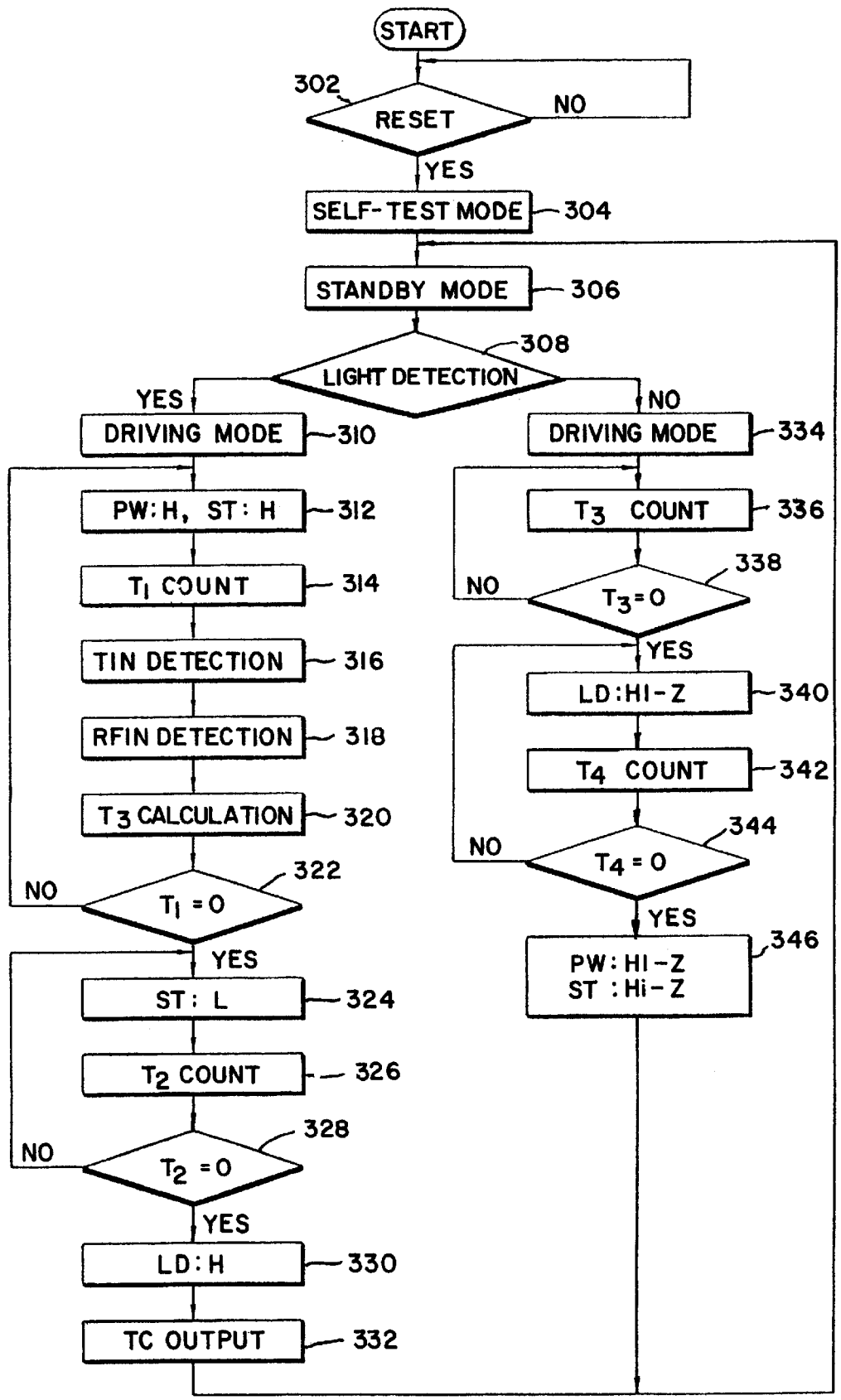
FIG. 4 is a flow chart illustrating an operation of a controller of the glare shielding device according to the preferred embodiment of the present invention.

The controller 140 includes a microprocessor or a microcomputer. An operation of the controller will be explained below in detail with reference to FIG. 4. As shown in FIG. 4, the controller 140 is reset by a reset pulse provided from the reset circuit 114 (step 302). When the reset signal is input, the controller 140 carries out a self-test mode (step 304). Thereafter, the controller 140 performs a standby mode (step 306). At this point, it makes to minimize power consumption that the controller 140 converts analog signals into digital signals during a standby mode. The welding light detection is carried out during a standby mode (step 308). At this time, when the welding light is detected, the standby mode changes to a driving mode in response to the PIN signal (step 310). When the driving mode is established, the PW and ST signals of a high state are output (step 312). The liquid crystal driving portion 130 is released from a floating state by the PW signal. A time T1 is counted (step 314), and then the TIN signal (step 316) and the RFIN signal (318) are detected. Subsequently, a liquid crystal off delay time T3 is calculated (step 320).

Next, whether a count value of T1 is "0" is checked (step 322). When the count value of T1 is "0", that is, when the set time T1 passes, the ST signal is changed from a high state to a low state (step 324), and a liquid crystal driving delay time T2 is counted (step 326). When the time T2 passes, the LD signal of a high state is output (step 330), and the TC signal is output (step 332). Finally, the controller is switched to a standby mode.

The liquid crystal activating portion 120 is operated by the LD signal of a high state, so that the liquid crystal panel 13 is activated. The TIN signal of a high state is output at a temperature of less than 0° C., and the TIN signal of a low state is output at a temperature of more than 0° C. When a temperature is less than 0° C., the activating voltage is compensated.

When the light detecting signal is not checked at the step 308, the controller is switched to a driving mode (step 334), and the liquid crystal off delay time T3 calculated at the step 320 is counted (step 336). When the time T3 passes (step 338), the LD signal that is a liquid crystal driving signal is switched from a high state to a low state (step 340), and a liquid crystal discharging time T4 is counted (step 342). When the time T4 passes, the PW and ST signals are switched to a Hi-Z state (step 346), bring about a standby mode.

As described above, since the controller is switched to a driving mode only during an AD action in which power consumption is relatively high and is in a standby mode during the rest mode, a power consumption can be minimized.

As described herein before, using the glare shielding device according to the preferred embodiment of the present invention, a power consumption can be minimized and worker can check a welding state during a welding process. Further, since by detecting an ambient temperature and compensating an activation voltage in light that response characteristics is lowered at a low temperature, an initial glare shielding effect can be improved.

While the invention has been particularly shown and described with reference to first preferred embodiment s thereof, it will be understood by those skilled in the art that the foregoing and other changes in form and details may be made therein without departing from the spirit and scope of the invention.

What is claimed is:

1. A glare shielding device for a welding helmet, comprising:

a liquid crystal panel;

a solar battery circuit for converting light into an electrical energy to output a first output voltage for maintaining driving of a liquid crystal of the liquid crystal panel and a second output voltage for activating the liquid crystal at initial state of operation of the liquid crystal;

a charging circuit for charging the first output voltage to provide a driving voltage;

an oscillator circuit for generating an oscillating signal in response to the second output voltage;

a high-voltage amplifier for charge-pumping the driving voltage in response to the oscillator circuit to generate a high voltage;

a regulator for regulating the high voltage to generate a stable driving voltage;

an activation voltage generator for generating a liquid crystal activation voltage in response to the oscillating signal;

a driving circuit power controller for generating a ground voltage by being switched from a standby mode to a driving mode in response to a light detecting signal, and for maintaining a floating state by being switched from the driving mode to the standby mode in response to a power off controlling signal;

a light detector for detecting a welding light using the second output voltage as a power source, and for outputting the light detection signal using the driving voltage as a power source;

a high-frequency detector for detecting a high-frequency generated during a welding process using the light detection signal as a power source, and for outputting a high-frequency detection signal using the liquid crystal driving control signal as a power source;

a liquid crystal activating portion for activating the liquid crystal panel using a minus voltage between the high voltage and the liquid crystal activation voltage in response to the light detection signal, and for maintaining an activation action during a predetermined period in response to the activation controlling signal;

a liquid crystal driving portion for driving the liquid crystal panel using a minus voltage between the liquid crystal driving voltage and a ground voltage in response to the oscillator circuit; and a controller for working in response to the light detection signal, for generating the activation controll signal during an initial activation time in response to the high-frequency detection signal, for generating the driving control signal after the initial activation time passes, for stopping generating the driving control signal and generating the power off control signal and performing the standby mode when the light detection signal and the high-frequency detection signal does not exist; and a temperature detector for detecting ambient temperature of the liquid crystal panel to lower the liquid crystal activation voltage when the ambient temperature is below about 0° C., whereby rapidly activating the liquid crystal panel.

2. The glare shielding device of claim 1, wherein the charging circuit comprise a charging battery for charging the first output voltage;

a plurality of light emitting diodes for being connected both terminals of the charging battery and preventing an overcharge; and a smooth capacitor for smootting an output voltage of the battery to output the driving voltage.

3. The glare shielding device of claim 1, wherein the regulator includes an adjusting means for adjusting a level of the liquid crystal driving voltage to adjust a light transmittance of the liquid crystal.

4. The glare shielding device of claim 1, wherein the activation voltage generator adjusts a level of the liquid crystal activation voltage in response to a temperature control signal, and the controller outputs the temperature control signal in response to a temperature detection of the temperature detector.

5. A method of controlling a glare shielding device for a welding helmet, comprising:

in a standby mode, generating first and second output voltages by converting ambient light into an electrical energy using a solar battery, generating a driving voltage of a predetermined level by charging the first output voltage, generating a high voltage and an activation voltage by charge-pumping the driving voltage in response to the second output voltage, and for maintaining a liquid crystal activating portion and a liquid crystal driving portion to be in a floating state until a power switch is turned off by a manual actuation;

detecting a welding light;

switching the liquid crystal activating portion and the liquid crystal driving portion to a driving mode by releasing the floating state, and activating a liquid crystal panel through the liquid crystal activating portion using a minus voltage between the high voltage and the activation voltage;

detecting a high frequency generated during a welding process;

driving the liquid crystal panel through the liquid crystal driving portion by finishing an activation time of the liquid crystal activating portion when the high frequency is detected; and switching the liquid crystal activating portion and the liquid crystal driving portion to the standby mode when the high frequency and the welding light are not detected.

6. The method of claim 5, wherein a level of the activation voltage varies according to an ambient temperature of the liquid crystal panel to rapidly activate the liquid crystal panel.

7. The method of claim 5, wherein the switching the liquid crystal activation portion and the liquid crystal driving portion to a driving mode is performed only when a power consumption of the glare shielding device reaches at a predetermined level, and wherein the switching the liquid crystal activation portion and the liquid crystal driving portion to the standby mode is performed when the level of the power consumption of the glare shielding device is lower than the predetermined level.

* * * * *